(12) United States Patent
Angot

(10) Patent No.: US 11,399,911 B2
(45) Date of Patent: Aug. 2, 2022

(54) TRAY FOR BAG FOR MEDICAL USE, TUBES AND ACCESSORIES, INTENDED FOR STERILISATION

(71) Applicant: TECHNOFLEX, Bidart (FR)

(72) Inventor: Maxime Angot, Ahetze (FR)

(73) Assignee: TECHNOFLEX, Bidart (FR)

( * ) Notice: Subject to any disclaimer, the term of this patent is extended or adjusted under 35 U.S.C. 154(b) by 0 days.

(21) Appl. No.: 17/048,122

(22) PCT Filed: Apr. 12, 2019

(86) PCT No.: PCT/EP2019/059429
§ 371 (c)(1),
(2) Date: Mar. 9, 2021

(87) PCT Pub. No.: WO2019/201776
PCT Pub. Date: Oct. 24, 2019

(65) Prior Publication Data
US 2021/0228302 A1    Jul. 29, 2021

(30) Foreign Application Priority Data
Apr. 16, 2018    (FR) ...................................... 1853309

(51) Int. Cl.
*A61B 50/33*    (2016.01)
*A61B 50/30*    (2016.01)

(52) U.S. Cl.
CPC ...... *A61B 50/33* (2016.02); *A61B 2050/3008* (2016.02)

(58) Field of Classification Search
CPC .................... A61B 50/33; A61B 2050/3008
(Continued)

(56) References Cited

U.S. PATENT DOCUMENTS 4,121,714 A * 10/1978 Daly .................... A61L 2/26
116/207
4,160,505 A *  7/1979 Rauschenberger . A61M 25/002
206/564

(Continued)

FOREIGN PATENT DOCUMENTS

| FR | 2699146 A1 | 6/1994 |
| GB | 2188549 A | 10/1987 |
| WO | 2014002938 A1 | 1/2014 |

OTHER PUBLICATIONS

International Search Report in co-pending, related PCT Application No. PCT/EP2019/059429, dated Jun. 6, 2019.
(Continued)

*Primary Examiner* — Jacob K Ackun
(74) *Attorney, Agent, or Firm* — Thomas | Horstemeyer, LLP

(57) ABSTRACT

The present invention concerns a shaped tray (10), comprising a plurality of housings (11, 12, 13), the tray (10) and each of said housings (11, 12, 13) being suitable for receiving a bag (20) for medical use, at least one tube (21) and at least one accessory (22), said bag (20) for medical use, said at least one tube (21) and said at least one accessory (22) being linked together, in which said tray (10) is suitable for being enclosed in a package (30) in order to carry out autoclaving, and it comprises cutouts at the bottom of same allowing possible condensates to flow out by force of gravity.

10 Claims, 4 Drawing Sheets

(58) Field of Classification Search
USPC .................................. 206/363, 364, 370
See application file for complete search history.

(56) References Cited

U.S. PATENT DOCUMENTS

| | | | | | |
|---|---|---|---|---|---|
| 4,482,053 | A | * | 11/1984 | Alpern | A61B 50/30 206/439 |
| 4,523,679 | A | * | 6/1985 | Paikoff | A61L 2/04 206/363 |
| 4,816,221 | A | * | 3/1989 | Harvey | A61L 2/07 156/281 |
| 4,863,016 | A | * | 9/1989 | Fong | A61M 25/002 206/210 |
| 5,165,539 | A | * | 11/1992 | Weber | A61B 50/33 206/363 |
| 6,193,932 | B1 | * | 2/2001 | Wu | A61L 2/07 206/210 |
| 6,663,829 | B1 | * | 12/2003 | Kjellstrand | A61J 1/2093 422/1 |
| 8,177,064 | B2 | * | 5/2012 | McCormick | A61B 50/33 206/370 |
| 2003/0192799 | A1 | * | 10/2003 | Addy | A61B 1/00144 206/364 |
| 2005/0189252 | A1 | * | 9/2005 | Naylor | A61B 50/36 206/439 |
| 2006/0283745 | A1 | * | 12/2006 | Massengale | A61M 25/002 206/438 |
| 2011/0229372 | A2 | * | 9/2011 | Whitehead | B31B 50/62 422/27 |
| 2011/0284410 | A1 | * | 11/2011 | Lockwood | B65D 21/0204 206/364 |
| 2016/0015456 | A1 | | 1/2016 | Lober | |
| 2017/0202699 | A1 | | 7/2017 | Zani et al. | |
| 2017/0290634 | A1 | | 10/2017 | Dacey | |

OTHER PUBLICATIONS

French Search Report in co-pending, related French Application No. 1853309, dated Jan. 10, 2019.

* cited by examiner

TRAY FOR BAG FOR MEDICAL USE, TUBES AND ACCESSORIES, INTENDED FOR STERILISATION

CROSS REFERENCE TO RELATED APPLICATIONS

This application is the 35 U.S.C. § 371 national stage application of PCT Application No. PCT/EP2019/059429, filed Apr. 12, 2019, which application claims the benefit of French Application No. FR 1853309, filed Apr. 16, 2018, both of which are hereby incorporated by reference herein in their entireties, including any figures, tables, nucleic acid sequence, amino acid sequences, or drawings.

FIELD OF THE INVENTION

The present invention relates to the field of packaging hollow and flexible systems sterilized by steam.

The present invention relates more particularly to a tray for a bag for medical use, tubings and accessories, intended to be sterilized by steam.

STATE OF THE ART

The following needs exist in the state of the art:

At the packing/packaging step, both:
Allowing ergonomic and repeatable positioning of the system (bag, tubings and accessories) in a peelable sterilization pouch.
Facilitating the stacking of several packed systems, by limiting the transmission of inter-system mechanical stresses.

At the sterilization step, both:
Allowing internal sterilization of the system.
Avoiding the transmission of mechanical stresses between the bag and the tubings and accessories, when the bag undergoes the possible inflations during the autoclave cycle (due to pressure variations in the autoclave).

The main issue is the preservation of the integrity of the system during autoclaving. It is all the more difficult to be preserved when the system contains:

A flexible bag potentially subject to inflation/deflation cycles,
PVC tubings, the mechanical strength of which decreases sharply at the autoclave temperature (121° C.),
Numerous injected plastic accessories, some of which can be relatively bulky and blunt.

There is no solution in the state of the art that allows preserving this integrity, in the case of "bags, tubings and accessories" systems as described above. The systems existing in the state of the art are directly packaged "in bulk" in a peelable autoclave pouch, without special precautions.

Bags for medical use in autoclavable packages composed of a layer made of transparent plastic film and of a paper layer permeable to water vapor are in particular known in the state of the art. Among these bags, some have tubes made of PVC material, but generally no bulky or blunt accessories.

Kits in packages of the type blister sterilized by irradiation or by ethylene oxide are also known in the state of the art. The lower part of these packages generally consists of a thermoformed polymer plate, the lid being flexible and peelable. Among these kits, some have tubes made of PVC material of different kinds and many injected rigid accessories, some of which are bulky and/or blunt.

DISCLOSURE OF THE INVENTION

The present invention intends to overcome the drawbacks of the prior art by proposing a shaped tray, including a plurality of housings, able to receive a bag for medical use, tubings and accessories, which are intended to be sterilized by steam.

To this end, the present invention relates, in its broadest sense, a shaped tray, including a plurality of housings, the tray and each of said housings being able to receive a bag for medical use, at least one tubing and at least one accessory, said bag for medical use, said at least one tubing and said at least one accessory being linked together, wherein said tray is able to be wrapped in a package for autoclaving.

Thus, the tray according to the present invention allows:
providing a lower horizontal bearing plane to lie flat;
embedding the tubings and accessories in depressed shapes, preserving them from any contact therebetween and with the bag;
providing a median horizontal bearing plane for the bag, allowing it to inflate slightly without stresses on the tubes or accessories;
providing an upper horizontal bearing plane to stack several packed systems (for example stacked "head to tail");
serving as a template, in particular to check, by visual inspection, that the system is correctly assembled.

The tray is made of polycarbonate.

The tray includes cutouts in its bottom allowing possible condensates to flow by gravity.

The peelable package includes an upper film made of transparent plastic material, and a lower film made of porous material.

Thus, the upper film allows visualization of the system in position in the tray, and the lower film allows circulation of steam and gravity discharge of the possible condensates.

Advantageously, at least one of said housings is configured to allow displacement of said at least one tubing in the axis of said at least one tubing.

Preferably, at least one of said housings is configured to prevent displacement of said at least one tubing in the axis normal to the plane of said tray.

According to one variant, at least one of said housings includes an abutment blocking said at least one tubing in one position, along an axis normal to the plane of said tray.

According to one embodiment, at least one of said housings is configured to block said at least one accessory in a predetermined position.

In one embodiment, said at least one tubing is free in displacement.

According to one embodiment, said tray includes planes, such as:
a housing able to receive said bag for medical use is located in a first plane;
two other housings able to receive said at least one tubing and said at least one accessory are located respectively in a second plane and in a third plane;
said first plane being distinct from said second and third planes and parallel to said second and third planes.

This allows increasing the compactness of the device while preserving the integrity of the kit.

According to another embodiment, said bag for medical use, said at least one tubing and said at least one accessory are located in the same plane.

Advantageously, said displacement of said at least one tubing in the axis of said at least one tubing has a length comprised between 5% and 25% of the length of said at least one tubing.

Preferably, said displacement of said at least one tubing in the axis of said at least one tubing has a length comprised between 10% and 20% of the length of said at least one tubing.

According to one variant, said tray is thermoformed.

According to another variant, said tray is produced by a plastic injection method.

According to another variant, said tray is obtained by stamping.

According to one embodiment, said tray is able to be stacked on another tray of the same type, while preserving the integrity of said bag for medical use.

According to one embodiment, at least one housing, able to receive said bag for medical use, is configured to allow the inflation of said bag for medical use.

According to a particular implementation, said package is peelable.

BRIEF DESCRIPTION OF THE DRAWINGS

The invention will be better understood with the description, given below for purely explanatory purposes, of an embodiment of the invention, with reference to the Figures in which.

DETAILED DESCRIPTION OF EMBODIMENTS OF THE INVENTION

Figure 1:
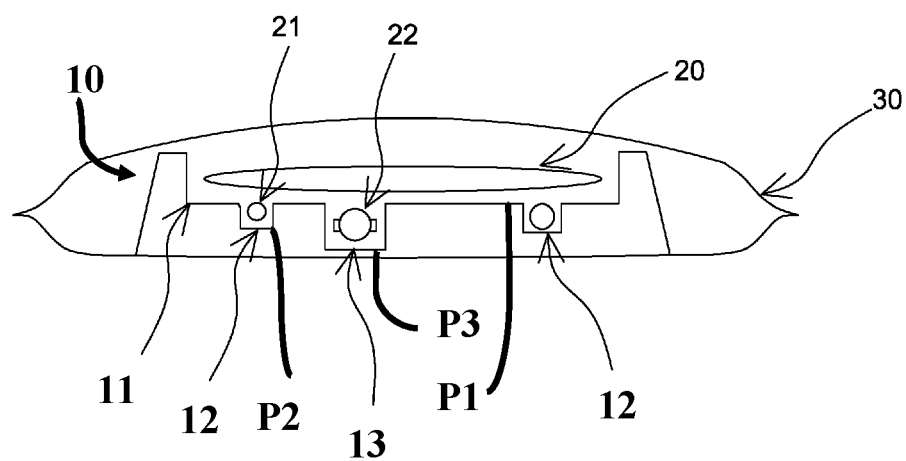
FIGS. 1, 2 and 3 illustrate the tray according to the present invention, in one embodiment.

The present invention relates to a shaped tray 10. The tray 10 according to the present invention includes a plurality of housings 11, 12, 13, the tray 10 and each of said housings 11, 12, 13 being able to receive a bag 20 for medical use, at least one tubing 21 and at least one accessory 22, said bag 20 for medical use, said at least one tubing 21 and said at least one accessory 22 being linked together. In addition, said tray 10 is able to be wrapped in a package 30 for autoclaving.

Figure 2:
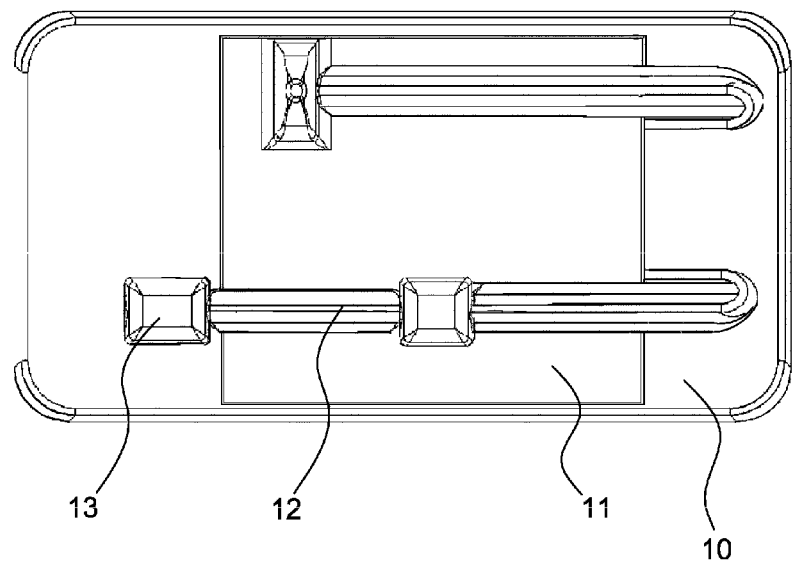
Figure 3:
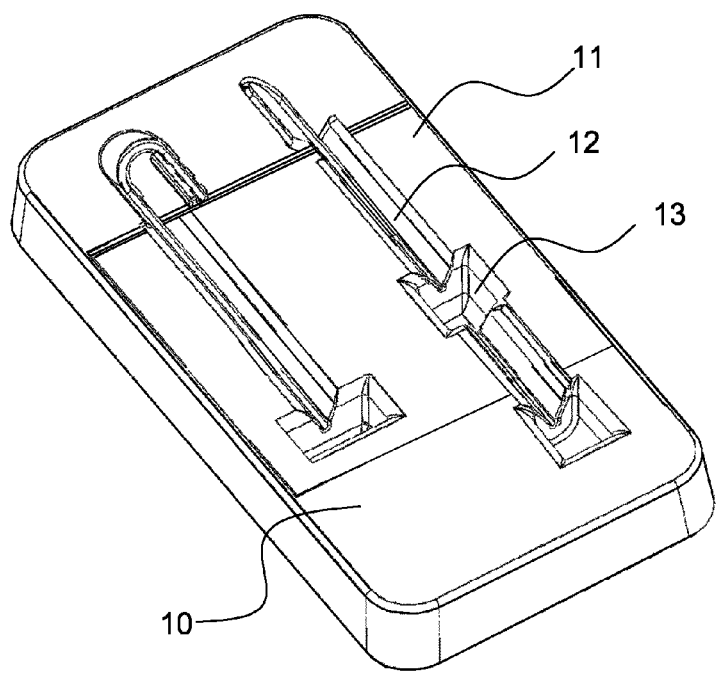

FIGS. 1, 2 and 3 illustrate an embodiment of the tray according to the present invention.

FIG. 1 shows the tray 10 which includes a plurality of housings 11, 12, 13. FIG. 1 also shows a bag 20 for medical use as well as tubings 21 and accessories 22, these different elements being linked together. Finally, FIG. 1 shows a package 30 which wraps the tray 10 according to the present invention.

The bag 20 and the tubings 21 are relatively free to move on the horizontal planes P1, P2, P3, in order to allow them to deform without resistance, in particular in the context of the inevitable shrinkages with some polymers at the mentioned temperatures.

FIGS. 2 and 3 also show the tray 10 which includes a plurality of housings 11, 12, 13.

Figure 4:
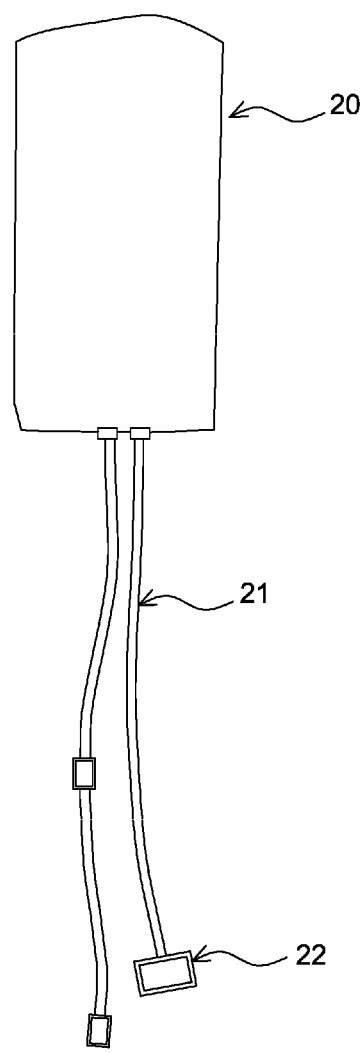
FIG. 4 represents a kit (bag for medical use, tubings and accessories) used in the context of the present invention.

FIG. 4 represents a kit (bag for medical use, tubings and accessories) used in the context of the present invention. The kit illustrated in FIG. 4 includes the bag 20 for medical use as well as the tubings 21 and the accessories 22, these different elements being linked together.

The autoclavable package 30 is used such that the upper film is made of transparent plastic material, thus allowing visualization of the system in position in the tray, and such that the lower film is made of porous material, paper type, allowing circulation of steam and gravity discharge of possible condensates.

The tray 10 is made of polycarbonate. The tray 10 is formed by thermoforming of a polycarbonate plate, which is a material that can withstand autoclaving at 121° C.

The tray 10 may include cutouts in its bottom allowing possible condensates to flow by gravity.

At least one of the housings 11, 12, 13 is configured to allow displacement of said at least one tubing 21 in the axis of said at least one tubing 21.

At least one of said housings 11, 12, 13 is configured to prevent displacement of said at least one tubing 21 in the axis normal to the plane of said tray 10.

At least one of said housings 11, 12, 13 includes an abutment blocking said at least one tubing 21 in one position, along an axis normal to the plane of said tray 10.

At least one of said housings 11, 12, 13 is configured to block said at least one accessory 22 in a predetermined position.

The at least one tubing 21 is free in displacement.

The tray 10 according to the present invention includes planes P1, P2, P3, such as:
 a housing 11 able to receive said bag 20 for medical use is located in a first plane P1;
 two other housings 12, 13 able to receive said at least one tubing 21 and said at least one accessory 22 are located respectively in a second plane P2 and in a third plane P3;
 and in that said first plane P1 is distinct from said second and third planes P2, P3 and parallel to said second and third planes P2, P3.

This allows increasing the compactness of the device, while preserving the integrity of the kit.

In another embodiment, said bag 20 for medical use, said at least one tubing 21 and said at least one accessory 22 are located in the same plane.

The displacement of said at least one tubing 21 in the axis of said at least one tubing 21 has a length comprised between 5% and 25% of the length of said at least one tubing 21.

In one embodiment, said displacement of said at least one tubing 21 in the axis of said at least one tubing 21 has a length comprised between 10% and 20% of the length of said at least one tubing 21.

As previously described, the tray 10 according to the present invention may be thermoformed.

In another embodiment, the tray 10 according to the present invention is made by a plastic injection method.

In another embodiment, the tray 10 according to the present invention is obtained by stamping.

The tray 10 according to the present invention is able to be stacked on another tray of the same type, while preserving the integrity of said bag 20 for medical use.

In one embodiment, at least one housing 11, 12, 13, able to receive said bag 20 for medical use, is configured to allow inflation of said bag 20 for medical use.

In one embodiment, said package 30 is peelable.

The tray 10 according to the present invention finds applications in the cases of steam-sterilization of hollow systems composed of fragile and deformable parts, and of rigid parts likely to mark or damage them.

The invention is described in the foregoing by way of example. It is understood that those skilled in the art is able to achieve different variants of the invention without however departing from the context of the patent.

The invention claimed is:
1. An assembly including:
 a sterilizable bag,
 a tubing connected to the sterilizable bag, a tray comprising an upper surface, a lower surface opposite the upper surface, a first recess in which the sterilizable bag is received, and a second recess in which the tubing is received, wherein the tubing is composed of PVC and varies in length when subjected to a sterilization process, the tubing being displaceable along a length-wise axis thereof within the second recess, and a package wrapping the tray, the package comprising an upper film made of transparent plastic material and a lower film made of porous material.

2. The assembly of claim 1, wherein the tray is made of polycarbonate.

3. The assembly of claim 1, wherein a length of displacement of the tubing within the second recess is decreased by between 5% and 25% of a length of the tubing.

4. The assembly of claim 1, wherein a length of displacement of the tubing within the second recess is decreased by between 10% and 20% of a length of the tubing.

5. The assembly of claim 1, wherein the tray is thermoformed.

6. The assembly of claim 1, wherein the tray is produced by a plastic injection method.

7. The assembly of claim 1, wherein the tray is produced by stamping.

8. The assembly of claim 1, wherein the first recess has a base lying in a plane recessed relative to a plane of the upper surface and the second recess has a base lying in a plane recessed relative to each of the plane of the upper surface and the plane of the first recess such that the bag disposed on the base of the first recess is positioned over the tubing disposed on the base of the second recess.

9. The assembly of claim 8, wherein the plane in which the base of the first recess lies extends parallel to the plane of the upper surface and the plane in which the base of the second recess lies.

10. The assembly of claim 8, wherein the tray comprises a third recess, the third recess having a base lying in a plane recessed relative to each of the plane of the upper surface of the tray, the plane of the first recess, and the plane of the second recess, and wherein the bag is positioned over the third recess.

* * * * *